United States Patent [19]
Smart

[11] Patent Number: 5,878,783
[45] Date of Patent: Mar. 9, 1999

[54] PIPELINE VEHICLE

[75] Inventor: Andrew Smart, Whickham, Great Britain

[73] Assignee: British Gas plc, London, Great Britain

[21] Appl. No.: 617,734

[22] Filed: Apr. 1, 1996

[30] Foreign Application Priority Data

May 22, 1995 [GB] United Kingdom .................. 95 10434

[51] Int. Cl.⁶ .................................................. F16L 55/12
[52] U.S. Cl. ............................ 138/93; 138/97; 104/138.2
[58] Field of Search ................................ 138/93, 97, 98; 104/138.2

[56] References Cited

U.S. PATENT DOCUMENTS

| | | | |
|---|---|---|---|
| 3,201,975 | 8/1965 | Cook | 138/97 |
| 3,547,040 | 12/1970 | Baran | 104/138.2 |
| 3,718,978 | 3/1973 | Van Koevering et al. | 138/97 |
| 3,753,766 | 8/1973 | Brown et al. | 138/97 |
| 4,006,359 | 2/1977 | Sullins et al. | 104/138.2 |
| 4,252,152 | 2/1981 | Martin et al. | 138/97 |
| 4,257,718 | 3/1981 | Rosa et al. | 405/167 |
| 4,443,948 | 4/1984 | Reeves . | |
| 4,447,777 | 5/1984 | Sharp et al. . | |
| 4,481,816 | 11/1984 | Prentice . | |
| 4,601,204 | 7/1986 | Fournot et al. . | |
| 4,621,532 | 11/1986 | Takagi et al. | 73/623 |
| 4,724,108 | 2/1988 | Jurgenlohmann et al. | 138/98 |
| 4,852,391 | 8/1989 | Ruch et al. . | |
| 4,941,511 | 7/1990 | Johansen et al. | 138/93 |
| 4,986,314 | 1/1991 | Himmler | 138/97 |
| 4,995,761 | 2/1991 | Barton | 138/98 |
| 5,190,705 | 3/1993 | Corazza | 138/97 |
| 5,197,540 | 3/1993 | Yagi et al. . | |
| 5,199,463 | 4/1993 | Lippiatt | 138/98 |
| 5,253,956 | 10/1993 | Fisco et al. | 138/97 |
| 5,284,096 | 2/1994 | Pelrine et al. | 104/138.2 |
| 5,309,844 | 5/1994 | Zollinger | 104/138.2 |
| 5,551,349 | 9/1996 | Bodzin | 104/138.2 |

FOREIGN PATENT DOCUMENTS

| | | |
|---|---|---|
| 40 24 926 | 2/1992 | Germany . |
| 2 147 080 | 5/1985 | United Kingdom . |
| 2 159 071 | 11/1985 | United Kingdom . |

*Primary Examiner*—Denise L. Ferensic
*Assistant Examiner*—James F. Hook
*Attorney, Agent, or Firm*—Oblon, Spivak, McClelland, Maier & Neustadt, P.C.

[57] ABSTRACT

An in-pipe vehicle for carrying out at least one operation in a pipeline. The vehicle comprises a train of modules 11–16 interlinked by suspension units 17 to allow serpentine movement through pipe bends. The vehicle train has its own internal power supply and drive mechanism in respective modules. A detector module 14 determines the presence of a service junction and a manipulative module 13 allows the vehicle to be temporarily wedged in the pipeline whilst providing rotational movement to facilitate the desired operation at the junction. This can include drilling and welding of a service pipe to the main using appropriate modules.

23 Claims, 3 Drawing Sheets

PIPELINE VEHICLE

The invention relates to an in-pipe vehicle which can carry out an operation within a pipeline, which pipeline may be a gas carrying pipeline.

There have been various activities undertaken concerned with pipeline inspection including remote cameras to enable information on the internal condition of pipelines to be obtained.

The present invention is concerned with an arrangement which will allow operations to be undertaken from within the pipeline, without the need for external drives, umbilicals or other connections which restrict the movement or utility of such arrangements.

According to the invention there is provided a pipeline vehicle comprising a plurality of linked modules forming a self powered train for travelling within a pipeline, at least one of the modules being capable of carrying out an operation on the pipeline.

Further according to the invention there is provided a method of effecting an operation on a pipeline comprising passing a vehicle consisting of a train of modules through the pipeline to detect the presence of an item to be operated on; and moving the vehicle to align a module with the item to carry out the desired operation.

The invention will now be described by way of example with reference to the accompanying drawings in which.

Figure 1:
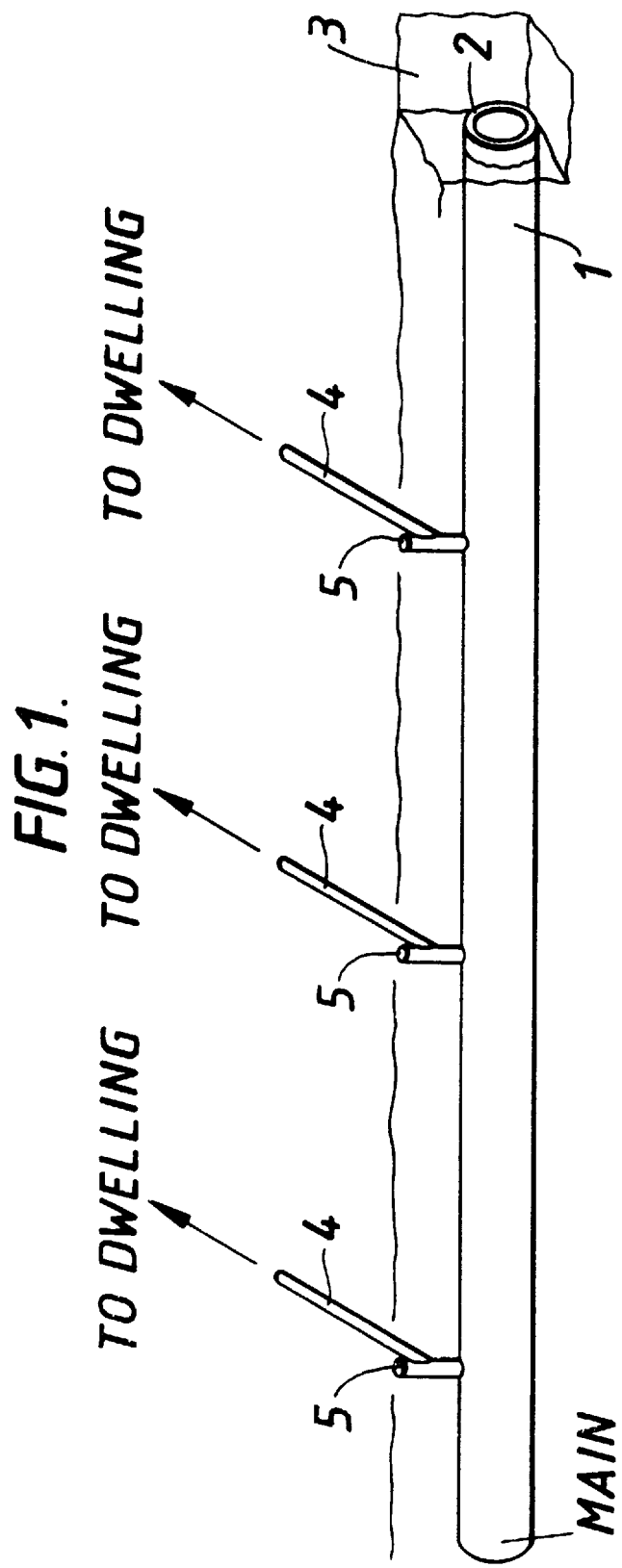
FIG. 1 shows a main pipeline with a number of service take-offs.

A buried cast iron gas main pipeline 1 shown in FIG. 1 carries a polyethylene pipe liner 2 which has previously been inserted through excavation 3 as part of a refurbishment programme.

A number of existing service pipe take-offs 4 each provide the source of gas to individual dwellings or other premises. As part of the refurbishment programme, there is a need to insert a liner in each service pipe and to join this to the main liner 2. In order to achieve this it has been necessary in the past to make an excavation at each service connection 5 (e.g. a screwed pipe connector or a service tee) and penetrate the main liner 2 through the excavation, sealing the take off to the main using a saddle connection, having removed part of the cast iron main in that region.

Figure 2:
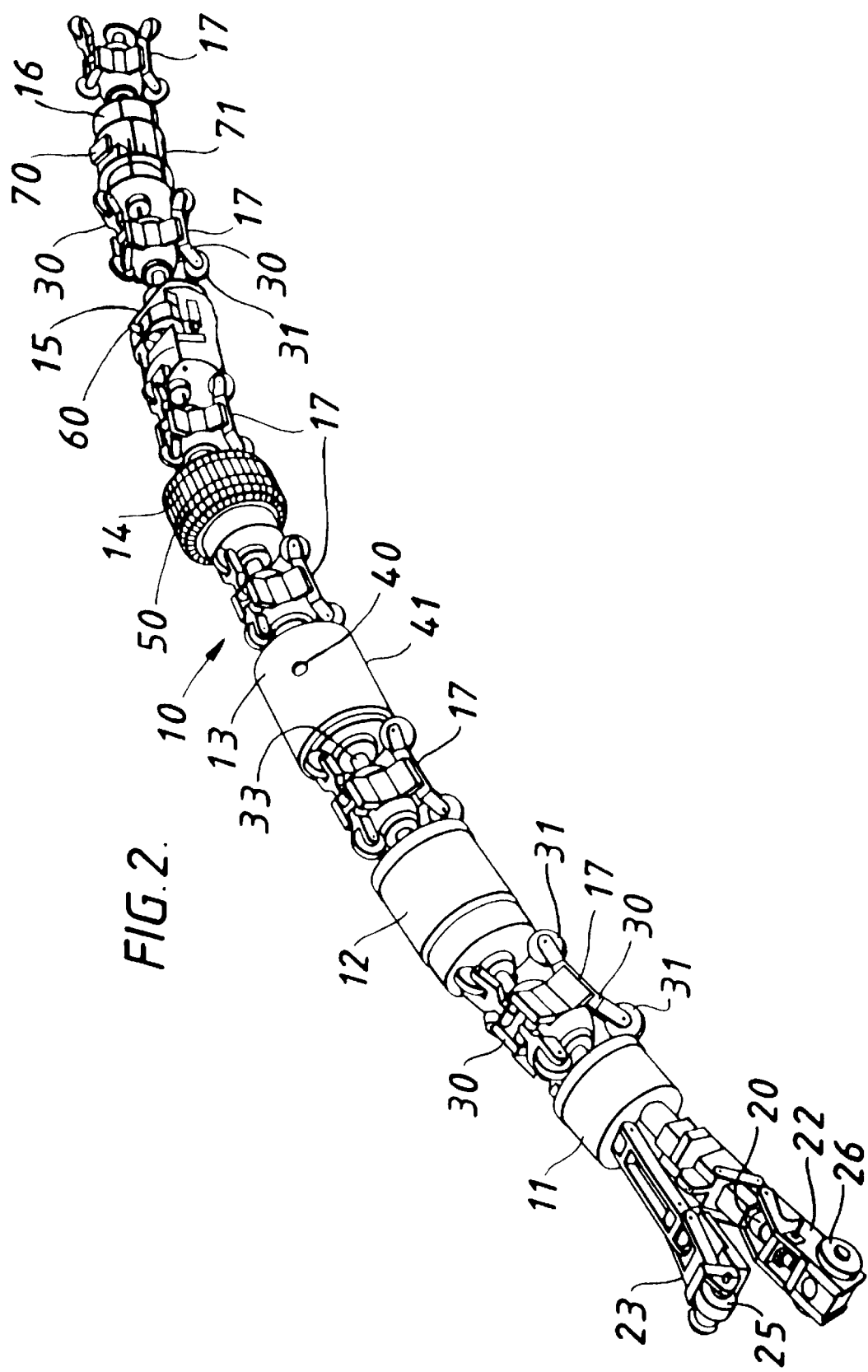
FIG. 2 shows an embodiment of the pipeline vehicle comprising a number of modules.

In the present invention, the need to have individual excavations is avoided as is the need to remove portions of the cast iron main at such excavations. FIG. 2 shows the mechanism now employed.

The in-pipe vehicle 10 of FIG. 2 includes a plurality of dissimilar individual modules 11–16 linked via similar linkage and suspension modules 17. The train of modular elements allows flexibility of operation in that each module provides a specific function which in this embodiment work together to remotely connect polyethylene gas main to service piping inserted into old metal piping (as described below). Other modular configurations would allow further tasks to be effected. The modular arrangement together with the suspension modules allows the degree of serpentine operation needed to negotiate bends in the pipe and to cope with the small diameter of the pipe which can be less than 150 mm.

The first module in the train is the traction module 11 which includes a motor 20 within one of the arms 22, 23 terminating in drive wheels 26 and idler wheels 25 respectively. The moveable arms 22 and 23 allow the wheels to contact closely the inner wall of the pipe through which it traverses and sensors within both the idler and drive wheel detect slippage which causes the traction unit to cause the arm to extend further to increase the traction affect. This can be effected by a motor driven ball screw acting on the lever arm to control the transverse load.

The motor 20 drives the wheels via gearing and feedback on movement, direction and slippage which can be compensated by internal control. Typically the traction unit provides a pushing force for the train of 80N at a speed of 30 mm/s. Power for the modules including the traction module 11 is provided by the power unit 12 which incorporates a number of rechargeable batteries. Electrical connection to the modules is provided via the suspension unit 17 connectors. The suspension units 17 are provided of common construction and placed between each functional module to give the train flexibility required for small pipes. Each module 17 includes three spring loaded arms 30 terminating in wheels 31. In order to avoid the use of highly preloaded suspension springs, the three lever arms at one end are interconnected via a slider. Thus when the body of the suspension unit is depressed below the pipe centre-line the wheels at the top will be pulled away from the wall to provide no resistance to the upward centralising force. A central shaft 33 through each suspension unit is free to rotate relative to the body. Connectors at each end allow electrical connection between all modules to be effected for power and intercommunication requirements.

The manipulator module 13 includes three retractable extenders 40 which are controlled to extend when required beyond the manipulator's cylindrical body 41 so as to firmly support the module as it becomes wedged in the pipe. A motor with associated gearing (e.g. ring gear) and feedback allows the rear portion of manipulator to rotate relative to the front portion and as the modules are all mechanically linked this causes modules connected to the rear of the manipulator to axially rotate within the pipe so that they can be aligned to a certain portion of the pipe to effect a task when required. A 'global' rotational manipulation for all modules has been found effective rather than each module making adjustments themselves, although 'local' manipulation may be required in addition for a given module. The rotational manipulation can provide two 210° arcs with the body clamped against the pipe wall. Electrical connection through the rotating interface within the manipulator is provided by use of a coiled cable to avoid slip ring interference and reduce module length.

The sensor module 14 includes a number of magnetic sensors 50 spaced around the periphery of the module. The sensors (typically 40 in number) form part of a variable reluctance magnetic circuit. The detectors can be of the Hall effect type.

As the vehicle moves into the region of a service pipe junction there will be a change in the magnetic field measurement. The hole in the offtake corresponds to the largest loss and indicates its position.

The drill module 15 includes a motorised drill bit 60 capable of drilling a hole through the pipe, but more typically through the pipe liner. A 16 mm hole would be suitable to access a 25 mm service pipe tee.

The fusion module 16 carries a sensor 70 (e.g. a force sensor with variable resistance when contacted by a guide wire) for detecting the guide wire in the service pipe liner (for reasons described below) and a heater device 71 for effecting a seal between the main liner and the service pipe liner. The manipulator module 13 allows the rotation by 180° of the train including module 16 to allow the sensing and sealing functions to be effected.

Figure 3:
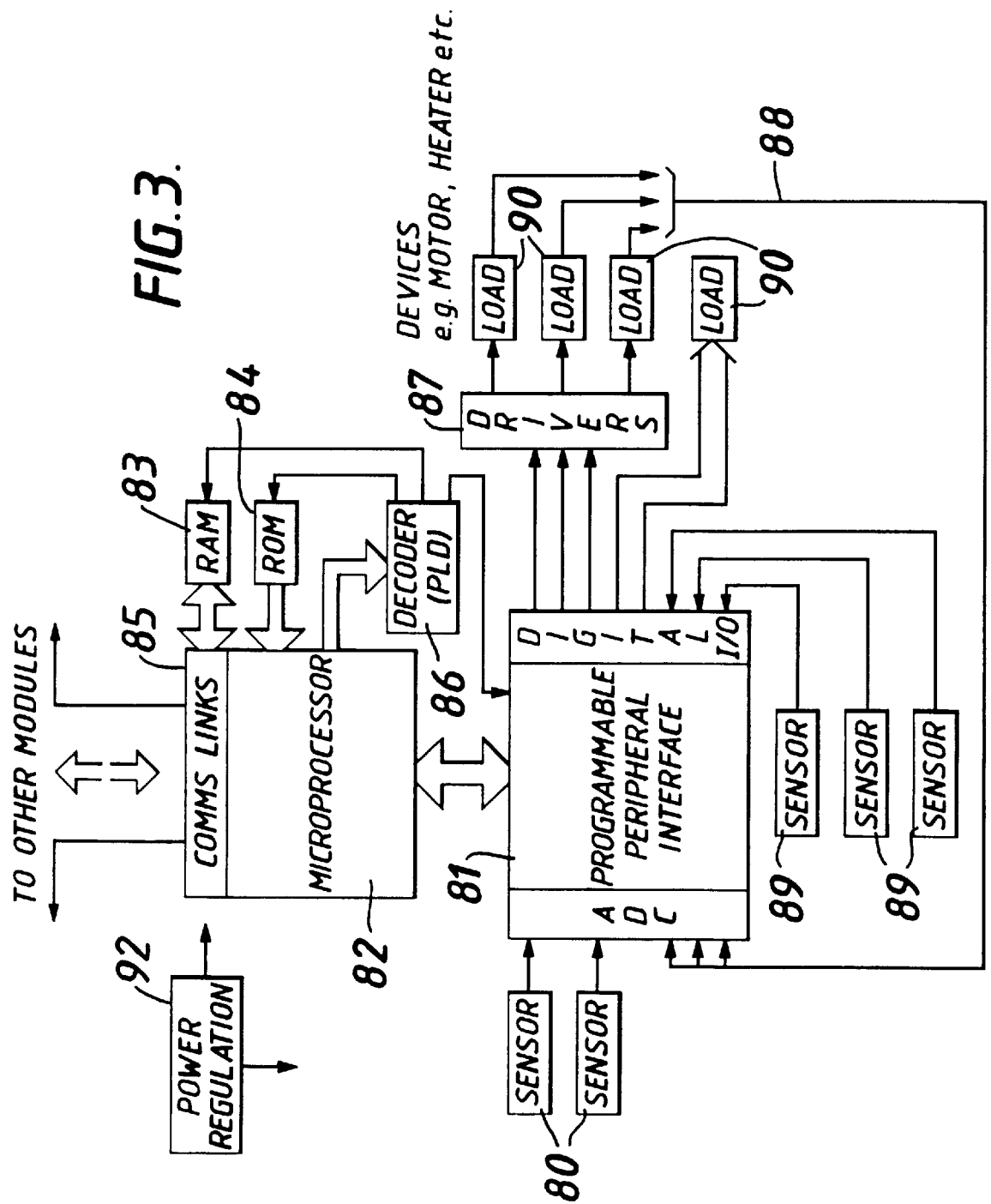
FIG. 3 shows the control mechanism associated with a module.

A master controller circuit can be located within the power module 12 and individual modules have localised control circuits to effect tasks associated with their particular devices. The master controller and the module controllers can be formed from a common approach using a hierarchial modular organisation of control and monitor process operating on independent communicating modules. The master controller is aware of operations being effected by individual modules and ensures the required tasks are carried out. Each module control arrangement includes a control board sensor and actuators of common hardware design with operation mode selection under software control. Such a module control system is shown in FIG. 3.

Analogue module sensors 80 connect to a programmeable peripheral interface 81 which carries an onboard analog to digital converter (ADC) and digital I/O lines. Digital sensors 89 connect to the digital inputs. Information from the interface is made available to microprocessor 82 which includes associated data storage RAM 83 and program storage ROM 84. A communication link 85 is also available to communicate with other modules. The microprocessor accesses sensor information via interface 81 (e.g. type HD631408) and controls the loads 90, (e.g. motors or other operational devices such as heaters) via decoder 86 and driver circuits 87. Current monitoring feedback is provided via line 88. Power supply regulation block 92 ensures trouble-free power supply requirements.

The microprocessor can be a T225 transputer contains a RISC CPU (16 bit 25 MHZ) and interprocessor communications links. Power for the devices can be high capacity nickel cadmium rechargeable batteries of the 'pancake' configuration.

The system can be sufficiently intelligent to carry out the tasks without external control although with a radio link (e.g. 1.394 GHZ) it is possible to send information on operations being effected to an 'above ground' station using the pipeline as a waveguide. Return signals could be sent to override or halt tasks if they are detected as being inappropriate. Hence automatic operation to effect an opening in the main liner would be carried out as follows.

The train of modules is driven by module 11 along the pipe until detector module 14 detects a service tee through the main liner. The aperture will typically be at the highest point in the pipe wall but the actual position is determined by the detectors. The train will then move on until the drill module 15 is at the correct position beneath the tee. The manipulator module 13 then activates its extenders 40 to clamp the module. If the drill is not determined to be in front of the aperture from earlier calculations, the module then rotates in an arc to line up the drill.

Following the drilling operation through the main liner, the manipulator module 13 retracts its extenders and the train moves forwards until the fusion module 16 is determined to be located beneath the service tee.

The manipulator module 13 again activates its extenders and clamps itself to the main pipe. A rotation of the module is effected if it is determined that this is necessary to locate the detector 70 in front of the tee. The hole already drilled in the main liner allows the service pipe liner to be inserted through the service pipe using a very flexible guide wire. The service liner has at its front end a tapered lead component formed from cross-linked polyethylene. The presence of the guide wire confirms to the detector that the correct service tee is being refurbished. Once the lead end is located in the drilled hole, the guide wire is removed, indicating that the jointing step can be effected. Thus the manipulator 13 rotates through 180° to locate the heater device 71 on the fusion module 16 adjacent to the region of the service liner end, within the main liner hole and electric power is applied to the heater to fuse the joint in the liners by raising the temperature to the crystalline melt stage, causing the service liner end-piece to expand and fuse simultaneously to the main liner.

The tasks for this service tee are now complete. The manipulator module contracts its extenders 40 and the train of modules moved on along the pipe until it detects the presence of the next service pipe, when the operations can proceed once again.

Because of the self powered, self controlled nature of the vehicle distances of 100 metres or more can be handled even with bends in the run.

I claim:

1. A pipeline vehicle comprising a plurality of linked modules forming a self powered and self controlled train for traveling within a pipeline without external control, at least one of the modules being capable of carrying out an operation on the pipeline, at a location of a branch pipeline; and wherein a module includes a hole forming tool provided to cause an aperture to be made through or into the pipe or a lining therein, at the location of the branch.

2. A vehicle as claimed in claim 1 wherein a module includes clamping means for holding the vehicle at a fixed point in the pipeline whilst rotational means are operable to rotate a cylindrical portion of the body of the module to align the module capable of carrying out the operation.

3. A vehicle as claimed in claim 1 including a module for detecting a branch.

4. A vehicle as claimed in claim 1 or 2 wherein one module includes magnetic detector means for detecting a pipe junction within the main pipeline.

5. A vehicle as claimed in claim 4 wherein the detector means includes a plurality of magnetic sensors spaced around the periphery of the module for detecting the relative circumferential position of the junction within the pipe.

6. A vehicle as claimed in claim 1 or 2 wherein said hole forming tool is a drill.

7. A vehicle as claimed in claim 6 wherein the drill is mounted to extend through a cylindrical wall portion of the module.

8. A vehicle as claimed in claim 1 or 2 wherein each of the modules is spaced from the next module and linked by an intermediate, flexibly mounted, wheeled carriage to allow serpentine travel through the pipeline.

9. A vehicle as claimed in claim 8 wherein the vehicle is constructed to travel through a pipe incorporating bends and having a diameter no more than 150 mm.

10. A vehicle as claimed in claim 1 including a computer device within a module for receiving an output from a plurality of sensors via interface means, said computer means being configured to automatically determine firstly when a pipe junction has been reached, secondly to determine the orientation of the junction, thirdly to determmine the amount of axial rotation and forward movement required to align the module capable of carrying out the operation on the pipeline.

11. A vehicle as claimed in claim 10 including transmitter means for communicating between the vehicle and the surface, said transmitter means being configured to use the pipeline as a waveguide.

12. A pipeline vehicle comprising:

a plurality of linked modules forming a self powered and self controlled train for traveling within a pipeline without external control, at least one of the modules being capable of carrying out an operation on the pipeline; and a traction module providing the driving power for the vehicle and including drive means for varying the degree of friction between the traction module and the pipe, dependent on slippage detection.

13. A vehicle as claimed in claim 12, further comprising slippage detection means, said slippage detection means including an idler wheel sensor communicating with an idler wheel and a drive wheel sensor communicating with a drive wheel.

14. A vehicle as claimed in claim 13, wherein said drive wheel and said idler wheel are mounted on moveable arms, and said drive moves said moveable arms so as to increase friction according to increases in slippage.

15. A pipeline vehicle comprising:

a plurality of linked modules forming a self powered and self controlled train for traveling within a pipeline without external control, at least one of the modules being capable of carrying out an operation on the pipeline;

wherein a module includes means for heating a plastic pipe to cause a fusion joint to be effected between a main pipe or liner and a smaller diameter plastic branch pipe extending therefrom.

16. A vehicle as claimed in claim 15, further comprising a heater device configured to effect a seal between a main liner and a branch pipe liner.

17. A method of effecting an operation on a pipeline comprising the steps of passing a self powered and self controlled vehicle comprising a train of modules through a main pipeline liner to automatically detect the presence of a branch pipeline;

automatically moving the vehicle to align a module with the branch pipeline without external control; and automatically aligning a sealing module in the pipe to seat a branch pipeline liner to the main pipe liner.

18. A method as claimed in claim 17, further comprising the step of:

heating an end of the branch pipeline liner, causing the end of the branch liner to expand and fuse to the main liner.

19. A method of effecting an operation on a pipeline comprising the steps of passing a self powered and self controlled vehicle comprising a train of modules through the pipeline to automatically detect the presence of a branch pipeline;

automatically moving the vehicle to align a module with the branch pipeline without external control; and forming an aperture through or into the pipe or a lining therein, at the location of the branch.

20. A method as claimed in claim 19 wherein the module for carrying out the operation is automatically moved longitudinally and axially to assist in alignment.

21. A method as claimed in claim 19 or 20 wherein said forming step comprises automatically aligning a drilling module in the pipe to form an aperture in a main pipe liner.

22. A method as claimed in claim 19 wherein the step of detecting the presence of an item to be operated on is effected by detecting magnetic changes in the pipeline by a plurality of magnetic sensors spaced around the periphery of a detector module.

23. A method as claimed in claim 19 including the steps of determining the orientation of the detected item and axially rotating a body portion of the module as part of the alignment procedure prior to carrying out the operation on the pipeline.

* * * * *